US008017312B2

(12) United States Patent
Cenatiempo et al.

(10) Patent No.: US 8,017,312 B2
(45) Date of Patent: Sep. 13, 2011

(54) METHOD FOR PRESERVING CELLS, TISSUES OR ORGANS USING A SOLUTION COMPRISING ALKYLDIAMINE-BETA-CYCLODEXTRIN

(75) Inventors: Yves Cenatiempo, Saint Julien l'Ars (FR); El Mustapha Belgsir, Poitiers (FR); Manilduth Ramnath, Buxerolles (FR); Frédéric Favreau, Coussay les Bois (FR); Michel Carretier, Cloue (FR); Gérard Mauco, Saint Benoit (FR); Thierry Hauet, Mignaloux Beauvoir (FR)

(73) Assignees: Biocydex, Poitiers (FR); Universite de Poitiers, Poitiers (FR); Centre Hospitalier Universitaire de Poitiers, Poitiers (FR); Institut National Sante Recherche Medicale, Paris (FR)

( * ) Notice: Subject to any disclaimer, the term of this patent is extended or adjusted under 35 U.S.C. 154(b) by 862 days.

(21) Appl. No.: 11/954,323

(22) Filed: Dec. 12, 2007

(65) Prior Publication Data

US 2009/0123904 A1    May 14, 2009

(30) Foreign Application Priority Data

Nov. 8, 2007   (FR) ...................................... 07 58881

(51) Int. Cl.
*A01N 1/00* (2006.01)
(52) U.S. Cl. ......................................................... 435/1.1
(58) Field of Classification Search .................. None
See application file for complete search history.

(56) References Cited

U.S. PATENT DOCUMENTS

| 4,879,283 | A | * | 11/1989 | Belzer et al. | .................... | 435/1.2 |
| 5,324,750 | A | * | 6/1994 | Lincoln et al. | ................ | 514/570 |
| 5,565,317 | A | * | 10/1996 | Dohi et al. | ........................ | 435/1.2 |
| 5,599,659 | A | * | 2/1997 | Brasile et al. | .................. | 435/1.1 |

FOREIGN PATENT DOCUMENTS

JP    57-177671    *    4/1981

OTHER PUBLICATIONS

Plin et al., "Resveratrol protects against cold ischemia-warm reoxygenation-induced damages to mitochondria and cells in rat liver", European J. Pharmacology 528 : 162-168 (2005).*
Bertacche et al., "Host-Guest Interaction Study of Resveratrol with Natural and Modified Cyclodextrins" J. Inclusion Phenomena Macrocyclic Chemistry 55 (3-4) : 279-287 (2006).*

* cited by examiner

*Primary Examiner* — Sandra Saucier
(74) *Attorney, Agent, or Firm* — Young & Thompson

(57) ABSTRACT

A composition for protecting and/or preserving cells, tissues or organs, includes at least one cyclodextrin, preferably closely combined with an antioxidant. A process for producing this composition and its uses are also disclosed.

10 Claims, No Drawings

METHOD FOR PRESERVING CELLS, TISSUES OR ORGANS USING A SOLUTION COMPRISING ALKYLDIAMINE-BETA-CYCLODEXTRIN

This invention relates to a composition for protection and preservation of organs, tissues or cells.

The invention also relates to a process for the production of this composition and its uses.

In numerous fields, in particular in cellular or tissue therapy, or for organ transplantation, it is essential to be able to correctly preserve and to keep viable cells, tissues or organs outside of an organism.

Actually, the conditions for preserving cells, tissues or organs during and after their sampling until their grafting play a key role for their functioning and their long-term viability.

It is known in particular that in the case of organ transplantation, more or less reversible tissue lesions appear during periods of hot and cold ischemia and worsen at the time of reperfusion, which can thus lead to chronic dysfunction of the grafts.

It is therefore necessary to use preservation solutions that can keep living cells in good condition, to protect them against the deleterious effects of a sampling and a graft, and to reduce the incidence of post-operatory complications.

In addition, whereby the entire transplantation process is frequently subjected to a time constraint, it is desirable that the preservation solutions allow the longest possible effective preservation.

A large number of preservation solutions currently exist. In particular, the solution of the University of Wisconsin, or UW or ViaSpan®, considered as the reference solution, is known. Other solutions have also been developed for about 15 years, such as IGL-1®, SCOT®, Celsior® or else Custodiol®.

Each of these solutions has different formulations and properties that are unique to them but none meets the above-mentioned requirement and none produces a truly satisfactory quality.

In addition, a shortage of donors exists, and one is increasingly confronted with marginal donors whose organs have to be preserved in an optimal way.

There is therefore a need to improve the existing solutions, in particular to make it possible to better preserve a cell, a tissue or an organ for a longer time and to restore its function more fully and more quickly after transplantation.

This is the purpose of this invention that proposes a composition for protecting and preserving cells, tissues or organs, comprising at least one cyclodextrin.

In particular, this invention aims at a solution that contains mineral salts, such as magnesium salts and/or selenium salts and/or zinc salts, for protecting and preserving cells, tissues or organs, comprising at least one cyclodextrin. Preferably, the cyclodextrin is closely combined with an antioxidant.

Closely combined is defined as interacting by any type of non-covalent bonding.

The antioxidant can be selected from among vitamin A, B, C or E, a flavonoid or a carotenoid such as beta-carotene or lycopene, or else a polyphenol such as curcumine.

The antioxidant is preferably resveratrol.

Resveratrol is a phytoallexin that is produced by certain plants in response to aggression by microorganisms. The best known producing plant is the grape-vine (*Vitis vinifera*), but there are other sources including the knotgrass of Japan (*Polygonum cuspidatum*), a plant that is used in traditional Asian pharmacopoeia.

The resveratrol is known as an antioxidant, but also as an anti-cancer, anti-metastatic, anti-inflammatory and anti-ageing agent.

The use of the resveratrol to protect the organs against deleterious effects of ischemia-reperfusion was considered in different publications, but no effective solution was proposed.

However, in a surprising way, a composition that comprises both a cyclodextrin and an anti-oxidant, in particular resveratrol, closely combined, has a very great effectiveness for protecting and preserving cells, tissues or organs.

Advantageously, the combination according to the invention makes it possible to protect, preserve and/or maintain organs, cells or tissues ex vivo, i.e., outside of a living organism.

It can also be used in the case of a graft as a supplementary therapeutic product for preserving cells, tissues or organs between the sampling on a donor and the graft on a receiver.

In particular, it can be used for the transplantation of organs in cold ischemia before reperfusion.

It can also be used in cellular therapy for preserving cells, for example stem cells, or in tissue therapy for preserving tissues.

According to another aspect, the composition according to the invention is useful for treating a donor or recipient of organs, tissues or cells.

The invention therefore also aims its use for the production of a medication that is designed to pretreat a donor or a recipient of organs, tissues or cells. Furthermore, the composition according to the invention is also useful for the production of a medication, for the post-treatment of a recipient and is intended to be administered to a person who has received a graft to extend the life of the graft(s).

The invention is now described in detail.

In this description, "cyclodextrin" is defined as any natural or modified cyclodextrin.

Advantageously, modified cyclodextrins are used.

In the case of monomodified cyclodextrins, the cyclodextrins that are modified on the primary hydroxyl—and in particular a 6A-(n-aminoalkylamino)-6A-deoxy-cyclomatoheptaose, such as the 6A-(3-aminopropylamino)-6A-deoxy-cyclomatoheptaose(propane diamine-β-CD) or the 6A-(2-aminoethylamino)-6A-deoxy-cyclomatoheptaose(ethane diamine-β-CD) described in the patent FR-2,714,067—are preferably selected.

According to an embodiment of the invention, the cyclodextrins are present in excess relative to the antioxidant. Preferably, the composition comprises an antioxidant/cyclodextrin molar ratio of between 1/1.5 and 1/150. Still more preferably, it comprises a resveratrol/cyclodextrin molar ratio of between 1/80 and 1/120.

The composition according to the invention can come in solid form, in particular in powder or pill form, or in liquid form as a concentrated solution to be diluted before or at the time of its use or a ready-to-use solution.

The pH of the composition is between 7.0 and 8.0, more particularly between 7.0 and 7.5.

Preferably, the composition according to the invention also comprises at least one impermeable agent and one buffer.

The impermeable agent can be selected from among the sugars, such as, for example, raffinose, saccharose, mannitol or glucose, or the anions such as citrate, gluconate or lactobionic acid. It makes it possible in particular to limit the cellular edemas that can take place during the hypothermic phases of preservation.

The buffer can be a bicarbonate, phosphate, histidine, HEPES or tryptophan buffer. It makes it possible to moderate the variations of the pH of the intravascular, interstitial and cellular compartments.

According to a particular embodiment, the composition according to the invention is a known composition, used for preserving cells, tissues and/or organs, to which are added at least one cyclodextrin and resveratrol and/or another antioxidant that is suitable for this invention.

The composition according to this invention can be obtained according to a process that comprises at least:
One stage for close combination (interaction by any type of non-covalent bonding) of a cyclodextrin with an antioxidant, and
One stage for adding the complex that is formed to the remainder of the composition.

According to one embodiment, the close combination stage between the cyclodextrin and the antioxidant can be carried out starting from their natural state, for example a solid powder-powder mixture.

Preferably, the close combination stage of the cyclodextrin with the antioxidant comprises the following stages:
Dissolving cyclodextrin in water,
Adding antioxidant in this solution,
Adjustment of the pH between 7 and 8,
Stirring, and
Optionally filtration of the solution optionally followed by a drying stage, preferably by freeze-drying.

The stage of adding the close cyclodextrin/antioxidant mixture to the remainder of the composition can consist in:
Adding it to other compounds, in particular mineral salts such as magnesium salts and/or selenium salts and/or zinc salts to form a solution for preserving cells, tissues, or organs, or
Introducing it into a known solution for preserving cells, tissues or organs, such as, for example, ViaSpan®, Custodiol®, or IGL-1®.

The cyclodextrin/antioxidant complex can be added in its solid form after drying or in its liquid form before drying.

According to a variant, the stage for adding the complex to the remainder of the composition can consist in introducing the close cyclodextrin/antioxidant combination into a mixture to produce a solution that is intended to be administered intravenously.

I. Composition Examples According to the Invention

These examples are solutions that consist of an organ preservation solution ViaSpan®, to which are added:
Either cyclodextrins only, namely propane diamine-β-CD,
Or a close propane diamine-β-CD/resveratrol mixture.

I.1 Solution 1: Propane Diamine-β-CD by Itself

The production process consists in taking up 15.77 mg of propane diamine-β-CD in powder form in 10 ml of the preservation medium ViaSpan® to obtain a 100×-concentrated solution.

Advantageously, the powder dissolves instantaneously because of the very soluble nature of the cyclodextrin.

I.2 Solution 2: Close Propane Diamine-β-CD/Resveratrol Mixture

In a first step, the production process consists in thoroughly mixing resveratrol molecules (supplied by ONCOPHYT) with propane diamine-β-CD molecules (produced by BIO-CYDEX), then in introducing the close mixture that is obtained into an organ preservation solution ViaSpan®.

The preparation of the close mixture is carried out according to the following operating procedure:
4.57 mg of resveratrol is added to 9 ml of a solution that contains 2495.3 mg of propane diamine-β-CD in water,
The pH is adjusted to 7.4,
The whole is stirred for 5 to 24 hours at 24° C. and in the absence of light,
The solution is next filtered in a Millipore hydrophilic PVDF filter and then freeze-dried to provide a powder that contains a close mixture whose resveratrol/propane diamine-β-CD molar ratio is 1/111,
The freeze-dried close mixture is preserved in amber bottles at 4° C.,
15.8 mg of the close mixture is then taken up in 10 ml of the ViaSpan® preservation medium to obtain a 100×-concentrated solution.

Advantageously, the powder dissolves instantaneously because of the masking of the hydrophic nature of the resveratrol by the cyclodextrin and the very soluble nature of the cyclodextrin.

II. Effects of the Composition According to the Invention

The composition according to the invention has been tested on preserving kidneys intended for transplantation.

The model best suited for the in vivo study of the preservation solutions with regard to kidney grafting is renal self-transplantation in swine.

This model consists in transplanting the left kidney in the same animal so as to study the effects of preservation and reperfusion without having the compatibility problems linked to the allotransplantation.

The left kidney is removed, preserved, then reimplanted. During the implantation of the left kidney, the right kidney is removed, which reproduces the human clinical situation where only the graft can ensure renal function.

The operating procedure is described below.

The left kidney is removed in the swine: it is rinsed, then preserved at 4° C. with a ViaSpan® preservation solution by itself, or the solution 1 of Example (I.1) or the solution 2 of Example (I.2).

The preservation period is 24 hours, the preservation time necessary for being able to measure a discriminating effect.

At the end of 24 hours, the kidney is retransplanted, and the animal is observed for a 3-month period.

The parameters that are studied are:
Renal function: urea and serum and urinary creatinine, analysis of the electrolyte composition of the blood and urinary ionogram, and proteinemia and proteinuria, and
Tissue development by a histological analysis; removal of samples by renal biopsy carried out 24 hours, 7 days and 1 month after transplantation, morphological study of these samples with observation of the appearance of tubular necrosis, inflammation, and the appearance of tubular atrophy,
The development of fibrosis, inflammation and tubular atrophy after the animal is sacrificed.

The results that relate to the resumption of diuresis obtained for three tests with each solution are presented in ml/24 hours in the following table:

| | Day | | | | | |
| --- | --- | --- | --- | --- | --- | --- |
| Diuresis in ml | D = 0 | D = 1 | D = 3 | D = 7 | D = 30 | D = 60 |
| ViaSpan ® | 2100 | 200 | 7600 | 7600 | 7067 | 6500 |
| Solution 1 (ViaSpan ® + Propane Diamine-β-CD) | 2300 | 850 | 2650 | 2350 | 3550 | / |

| Diuresis in ml | D = 0 | D = 1 | D = 3 | D = 7 | D = 30 | D = 60 |
|---|---|---|---|---|---|---|
| Solution 2 (ViaSpan® + Propane Diamine-β-CD + Resveratrol) | 2150 | 1700 | 4700 | 4100 | 5600 | 3650 |

It is noted that the use of the compositions according to the invention makes it possible to considerably improve the resumption of diuresis (D=1) relative to the reference solution ViaSpan®.

It is also observed that the polyurea profile following preservation and transplantation (starting from D=3) is better controlled during the use of the compositions according to the invention. The reconstitution of the uremia is also faster.

Relative to the plasmatic creatinine, the results that are obtained are grouped in the following table. This table also comprises comparison results that are produced with an IGL-1® solution that is obtained from the publication <<*Evaluation de IGL-1, une nouvelle solution de conservation d'organes: résultats pré-cliniques en transplantation rénale* [Evaluation of IGL-1, A New Solution for Organ Preservation: Preclinical Results in Renal Transplantation]>>, Bardet et al., *Progrès en Urologie* [Advances in Urology] (2005), 15, 481-488.

| Creatinine in μmol · L⁻¹ | D = 0 | D = 1 | D = 3 | D = 14 | D = 30 | D = 60 |
|---|---|---|---|---|---|---|
| ViaSpan® | 85 | 637 | 605 | 312 | 235 | 207 |
| IGL-1® | 100 | 500 | 210 | / | / | / |
| Solution 1 (ViaSpan® + Propane Diamine-β-CD) | 62 | 309 | 160 | 133 | | |
| Solution 2 (ViaSpan® + Propane Diamine-β-CD + Resveratrol) | 87 | 260 | 139 | 122 | 127 | 131 |

It is noted that the compositions according to the invention (solution 1 and solution 2) make it possible to reduce the plasmatic creatinine effectively after transplantation of the kidney comparatively to the reference solution ViaSpan® or the solution IGL-1®.

Relative to the proteinuria, the results that are obtained are grouped in the following table:

| Proteinuria en g | D = 0 | D = 1 | D = 3 | D = 14 | D = 30 | D = 60 |
|---|---|---|---|---|---|---|
| ViaSpan® | 0.12 | 3.37 | 1.97 | 1.80 | 2.20 | 2.53 |
| Solution 1 (Viaspan® + Propane Diamine-β-CD) | 0.18 | 0.80 | 0.15 | 0.12 | / | / |
| Solution 2 (Viaspan® + Propane Diamine-β-CD + Resveratrol) | 0.09 | 2.46 | 0.25 | 0.10 | 0.20 | 0.23 |

There again it is noted that the use of the compositions according to the invention makes it possible to control the proteinuria levels in a considerably better fashion.

Furthermore, the histological study shows that the use of the compositions according to the invention significantly reduces the expression of the Type II major histocompatibility complex (MHC) and reduces the markers of apoptosis and fibrosis.

Of course, the invention obviously is not limited to the examples that are shown and described above, but on the contrary covers all the variants, in particular regarding the total content of the compositions and their production processes.

The invention claimed is:

1. A method of protecting, preserving and/or maintaining organs, tissues or cells ex vivo, comprising preserving the organs, tissues or cells with an effective amount of a composition comprising 6A-[(n-aminoalkyl)amino]-6A-deoxy-β-cyclodextrin.

2. The method of claim 1, wherein the composition comprises the cyclodextrin closely combined with an antioxidant.

3. The method of claim 2, wherein the antioxidant is resveratrol.

4. The method of claim 2, wherein the antioxidant is curcumine.

5. The method of claim 2, wherein the composition comprises an antioxidant/cyclodextrin molar ratio of between 1/1.5 and 1/150.

6. The method of claim 5, wherein the antioxidant is resveratrol.

7. The method of claim 5, wherein the antioxidant is curcumine.

8. The method of claim 1, wherein the composition further comprises an impermeable agent and a buffer.

9. The method of claim 1, wherein the organs are preserved in cold ischemia.

10. The method according to claim 1, wherein the composition comprises 6A-[(3-aminopropyl)amino]-6A-deoxy-β-cyclodextrin, or 6A-[(2-aminoethyl)amino]-6A-deoxy-β-cyclodextrin, or a combination thereof.

* * * * *